US011536676B2

(12) United States Patent
Chillara et al.

(10) Patent No.: US 11,536,676 B2
(45) Date of Patent: Dec. 27, 2022

(54) CHARACTERIZATION OF FLUID INSIDE PIPE USING MULTI FREQUENCY ELECTRICAL SIGNAL

(71) Applicants: Triad National Security, LLC, Los Alamos, NM (US); Chevron U.S.A. Inc., San Ramon, CA (US)

(72) Inventors: Vamshi Krishna Chillara, Los Alamos, NM (US); Maruti Kumar Mudunuru, Los Alamos, NM (US); Hari Selvi Viswanathan, Los Alamos, NM (US); Satish Karra, Los Alamos, NM (US); Bulbul Ahmmed, Los Alamos, NM (US); Jeffrey Foering App, Houston, TX (US); Gary Michael Hoversten, Los Alamos, NM (US)

(73) Assignees: Triad National Security, LLC, Los Alamos, NM (US); Chevron U.S.A. Inc., San Ramon, CA (US)

( * ) Notice: Subject to any disclaimer, the term of this patent is extended or adjusted under 35 U.S.C. 154(b) by 172 days.

(21) Appl. No.: 16/948,851

(22) Filed: Oct. 2, 2020

(65) Prior Publication Data

US 2022/0107283 A1    Apr. 7, 2022

(51) Int. Cl.
    *G01N 27/02* (2006.01)
    *G01N 33/28* (2006.01)
(52) U.S. Cl.
    CPC ....... *G01N 27/028* (2013.01); *G01N 33/2823* (2013.01)

(58) Field of Classification Search
    CPC . G01N 27/028; G01N 33/2823; G01N 27/026
    See application file for complete search history.

(56) References Cited

U.S. PATENT DOCUMENTS

| | | | |
|---|---|---|---|
| 6,147,497 A | 11/2000 | Berryman | |
| 6,940,286 B2 | 9/2005 | Wang | |
| 7,673,682 B2 | 3/2010 | Daily | |
| 10,823,869 B2 * | 11/2020 | Capoglu | E21B 47/113 |
| 11,090,929 B2 * | 8/2021 | Chen | B41J 2/1631 |
| 11,249,217 B2 * | 2/2022 | Guner | E21B 47/0025 |
| 11,293,279 B1 * | 4/2022 | Karra | G01V 3/24 |
| 2016/0097876 A1 | 4/2016 | Freed | |
| 2016/0356911 A1 | 12/2016 | Wilson | |
| 2018/0120269 A1 * | 5/2018 | Sinha | G01N 29/343 |

(Continued)

FOREIGN PATENT DOCUMENTS

| | | |
|---|---|---|
| DE | 102006049554 A1 | 4/2008 |
| EP | 3126787 A2 | 2/2017 |
| WO | 2004021880 A1 | 3/2004 |

*Primary Examiner* — Alvaro E Fortich
*Assistant Examiner* — Zannatul Ferdous
(74) *Attorney, Agent, or Firm* — Esplin & Associates, PC

(57) ABSTRACT

A multi-frequency signal may be used to induce voltage difference across a portion of a pipe. The voltage difference may be induced to take multi-frequency measurement of impedance characteristics of fluid inside the pipe. The multi-frequency measurement of the impedance characteristic of the fluid inside the pipe may be used to determine a characteristic of the fluid inside the pipe. This may be achieved by active integration of experimental data with high-resolution multi-frequency electrical impedance tomography (MFEIT) modeling.

20 Claims, 11 Drawing Sheets

(56) References Cited

U.S. PATENT DOCUMENTS

| | | | |
|---|---|---|---|
| 2018/0128993 A1* | 5/2018 | Brown | G02B 6/3866 |
| 2018/0164466 A1 | 6/2018 | Zhang | |
| 2021/0072137 A1* | 3/2021 | Michel | G01N 15/1031 |

* cited by examiner

CHARACTERIZATION OF FLUID INSIDE PIPE USING MULTI FREQUENCY ELECTRICAL SIGNAL

ACKNOWLEDGEMENT OF GOVERNMENT SUPPORT

The United States government has certain rights in this invention pursuant to Contract No. 89233218CNA000001 between the United States Department of Energy and TRIAD National Security, LLC for the operation of Los Alamos National Laboratory.

PARTIES TO JOINT RESEARCH AGREEMENT

The research work described here was performed under a Cooperative Research and Development Agreement (CRADA) between Los Alamos National Laboratory (LANL) and Chevron under the LANL-Chevron Alliance, CRADA number LA05C10518.

TECHNICAL FIELD

The present disclosure relates generally to the field of fluid characterization using multi-frequency measurement of impedance characteristic of fluid inside a pipe.

BACKGROUND

A horizontal well may include multiple potential production stages. Determining characteristics of fluid flow inside the horizontal well to identify which stages are producing oil is challenging.

SUMMARY

This disclosure relates to determining fluid characteristics. A set of electrodes may be configured to measure one or more impedance characteristics of fluid inside a pipe. The set of electrodes may include a first electrode positioned at a first location along the pipe, a second electrode positioned at a second location along the pipe, and/or other electrodes. A signal generator may be configured to generate one or more multi-frequency signals. The multi-frequency signal(s) may induce voltage difference between the first location along the pipe and the second location along the pipe. The voltage difference may be induced for multi-frequency measurement of the impedance characteristic(s) of the fluid inside the pipe. The multi-frequency measurement of the impedance characteristic(s) of the fluid inside the pipe may be obtained from the set of electrodes. One or more characteristics of the fluid inside the pipe may be determined based on the multi-frequency measurement of the impedance characteristic(s) of the fluid inside the pipe and/or other information.

A system that determines fluid characteristics may include one or more electronic storage, one or more sets of electrodes, one or more signal generators, one or more processors, and/or other components. The electronic storage may store information relating to electrode, information relating to impedance characteristic, information relating to fluid, information relating to pipe, information relating to signal generator, information relating to multi-frequency signal, information relating to multi-frequency measurement of impedance characteristic, and/or other information.

The set(s) of electrodes may be configured to measure one or more impedance characteristics of fluid inside a pipe. The set of electrodes may include multiple electrodes positioned at different locations along the pipe. The set of electrodes may include a first electrode positioned at a first location along the pipe, a second electrode positioned at a second location along the pipe, and/or other electrodes positioned at other locations along the pipe.

In some implementations, an impedance characteristic of the fluid inside the pipe measured by a set of electrodes may include voltage difference between different locations along the pipe. An impedance characteristic of the fluid inside the pipe measured by a set of electrodes may include voltage difference between the first location along the pipe and the second location along the pipe.

In some implementations, an impedance characteristic of the fluid inside the pipe measured by a set of electrodes may include current between different locations along the pipe. An impedance characteristic of the fluid inside the pipe measured by a set of electrodes may include current between the first location along the pipe and the second location along the pipe.

The signal generator(s) may be configured to generate one or more multi-frequency signals. The multi-frequency signal(s) may induce voltage difference between different locations along the pipe. The multi-frequency signal(s) may include voltage difference between the first location along the pipe and the second location along the pipe, and/or other locations along the pipe. The voltage difference may be induced for multi-frequency measurement of the impedance characteristic(s) of the fluid inside the pipe.

In some implementations, a multi-frequency signal may include a voltage chirp signal. In some implementations, a multi-frequency signal may include a current chirp signal.

The processor(s) may be configured by machine-readable instructions. Executing the machine-readable instructions may cause the processor(s) to facilitate determining fluid characteristics. The machine-readable instructions may include one or more computer program components. The computer program components may include one or more of a measurement component, a characteristic component, and/or other computer program components.

The measurement component may be configured to obtain the multi-frequency measurement of the impedance characteristic(s) of the fluid inside the pipe. The multi-frequency measurement of the impedance characteristic(s) of the fluid inside the pipe may be obtained from the set of electrodes and/or other locations.

The characteristic component may be configured to determine one or more characteristics of the fluid inside the pipe. The characteristic(s) of the fluid inside the pipe may be determined based on the multi-frequency measurement of the impedance characteristic(s) of the fluid inside the pipe and/or other information.

In some implementations, a characteristic of the fluid inside the pipe determined based on the multi-frequency measurement of the impedance characteristic(s) of the fluid inside the pipe may include fluid composition, fluid flow regime, and/or other characteristic. In some implementations, the fluid composition may include percentage of oil, water, and/or other composition in the fluid. In some implementations, the fluid flow regime may include stratified flow, bubbly flow, slug flow, and/or other types of flow.

In some implementations, the characteristic(s) of the fluid inside the pipe determined for different times may be used to determine one or more dynamic characteristics of the fluid inside the pipe.

In some implementations, the pipe may be inside a horizontal well, and the characteristic(s) of the fluid inside the pipe determined for different locations may be used to identify producing stages and non-producing stages inside the horizontal well.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

DETAILED DESCRIPTION

The present disclosure relates to determining fluid characteristics. A multi-frequency signal may be used to induce voltage difference across a portion of a pipe. The voltage difference may be induced to take multi-frequency measurement of impedance characteristics of fluid inside the pipe. The multi-frequency measurement of the impedance characteristic of the fluid inside the pipe may be used to determine a characteristic of the fluid inside the pipe. This may be achieved by active integration of experimental data with multi-frequency electrical impedance tomography (MFEIT) modeling.

Figure 1:
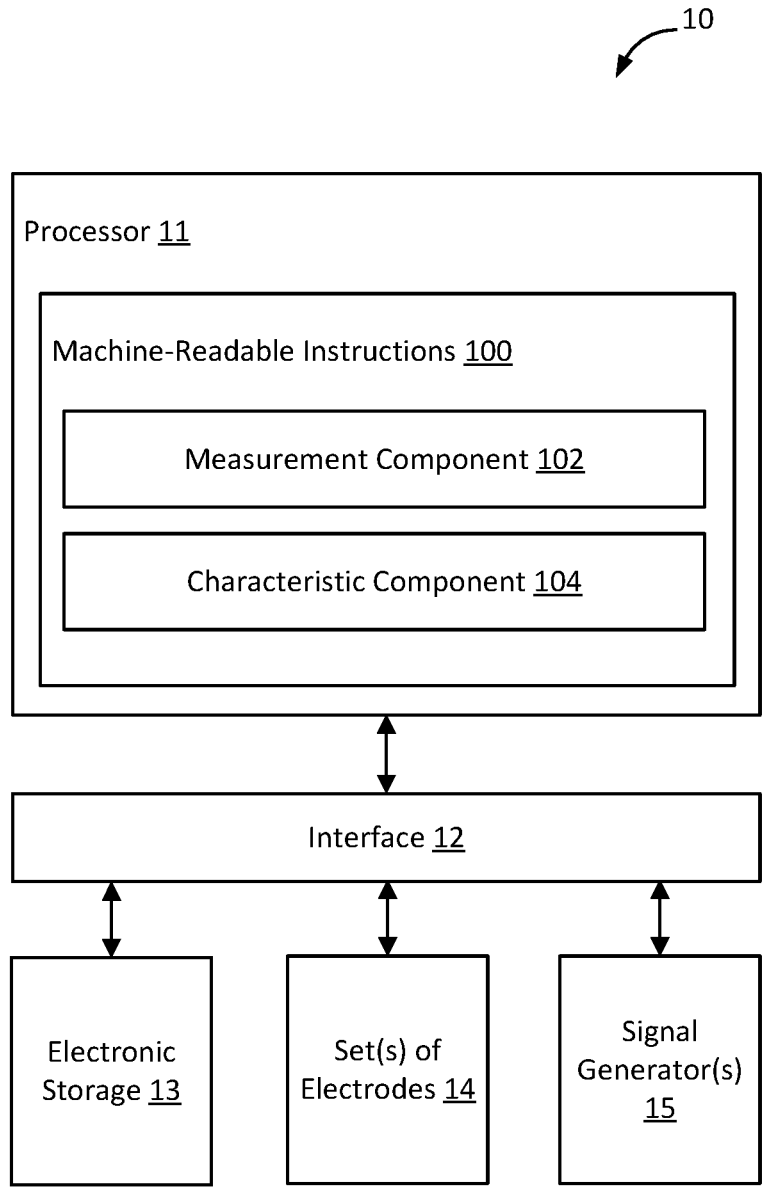
FIG. 1 illustrates an example system that determines fluid characteristics.

The methods and systems of the present disclosure may be implemented by and/or in a computing system, such as a system 10 shown in FIG. 1. The system 10 may include one or more processors 11, an interface 12 (e.g., bus, wireless interface), an electronic storage 13, one or more sets of electrodes 14, one or more signal generators 15, and/or other components. In some implementations, one or more components of the system 10 may be separate from the system 10. For example, the signal generator(s) 15 may be separate from the system 10 and may be controlled by one or more processors separate from the processor 11.

The set(s) of electrodes 14 may be configured to measure one or more impedance characteristics of fluid inside a pipe. The set(s) of electrodes 14 may include a first electrode positioned at a first location along the pipe, a second electrode positioned at a second location along the pipe, and/or other electrodes. The signal generator(s) 15 may be configured to generate one or more multi-frequency signals. The multi-frequency signal(s) may induce voltage difference between different locations along the pipe, such as between the first location along the pipe and the second location along the pipe. The voltage difference may be induced for multi-frequency measurement of the impedance characteristic(s) of the fluid inside the pipe by the set(s) of electrodes 14. The multi-frequency measurement of the impedance characteristic(s) of the fluid inside the pipe may be obtained by the processor 11 from the set(s) of electrodes 14. One or more characteristics of the fluid inside the pipe may be determined by the processor 11 based on the multi-frequency measurement of the impedance characteristic(s) of the fluid inside the pipe and/or other information.

A pipe may refer to a hollow object used for conveyance of material. A pipe may be constructed from metallic and/or non-metallic material. A pipe may be used to convey fluid, such as oil, water, or oil-water mixture, from one location to another location. A pipe may be located inside a well, such as a horizontal well, a vertical well, a deviated well, and/or other types of well. For instance, a pipe may refer to a casing (e.g., conductor casing, surface casing, intermediate casing, production casing) inside a well. Fluid may refer to substance that has no fixed shape. Fluid may refer to substance that yields easily to external pressure. Fluid may be composed of a single type of substance or multiple types of substance. For example, fluid may include oil-water-gas mixtures. Other types of fluid are contemplated.

The set(s) of electrodes 14 may include one or more electrodes. An electrode may refer to an electric conductor, such as a solid electric conductor. An electrode may carry electric current into one or more materials, such as solid and/or liquid materials. An electrode may be used to make contact with the pipe, the fluid inside the pipe, and/or other materials around/in the pipe.

The set(s) of electrodes 14 may be positioned within the inner volume of the pipe, within the material of the pipe, on the inner surface of the pipe, on the outer surface of the pipe, and/or outside the pipe. The set(s) of electrodes 14 may be positioned with respect to the pipe so that the set(s) of electrodes 14 make contact with the pipe. For example, the set(s) of electrodes 14 may be conductively coupled to the pipe. In some implementations, the pipe itself and/or one or more portions of the pipe may form the set(s) of electrodes. The set(s) of electrodes 14 may be positioned with respect to the pipe so that the set(s) of electrodes 14 do not make contact with the pipe. For example, the set(s) of electrodes 14 may not be conductively coupled to the pipe. For instance, the set(s) of electrodes be conductively insulated from the pipe.

The set(s) of electrodes 14 may be positioned with respect to the pipe so that the set(s) of electrodes 14 make contact with the fluid inside the pipe. For example, the set(s) of electrodes 14 may be conductively coupled to the fluid inside the pipe. The set(s) of electrodes 14 may be positioned with respect to the pipe so that the set(s) of electrodes 14 do not make contact with the fluid inside the pipe. For example, the set(s) of electrodes 14 may not be conductively coupled to the fluid inside the pipe.

The set(s) of electrodes 14 may include multiple electrodes positioned at different locations along the pipe. The set of electrodes may include a first electrode positioned at a first location along the pipe, a second electrode positioned at a second location along the pipe, and/or other electrodes positioned at other locations along the pipe. Electrodes being positioned at different locations along the pipe may include the electrodes being positions at different locations within the inner volume of the pipe, within the material of the pipe, on the inner surface of the pipe, on the outer surface of the pipe, and/or outside the pipe.

Figure 3:
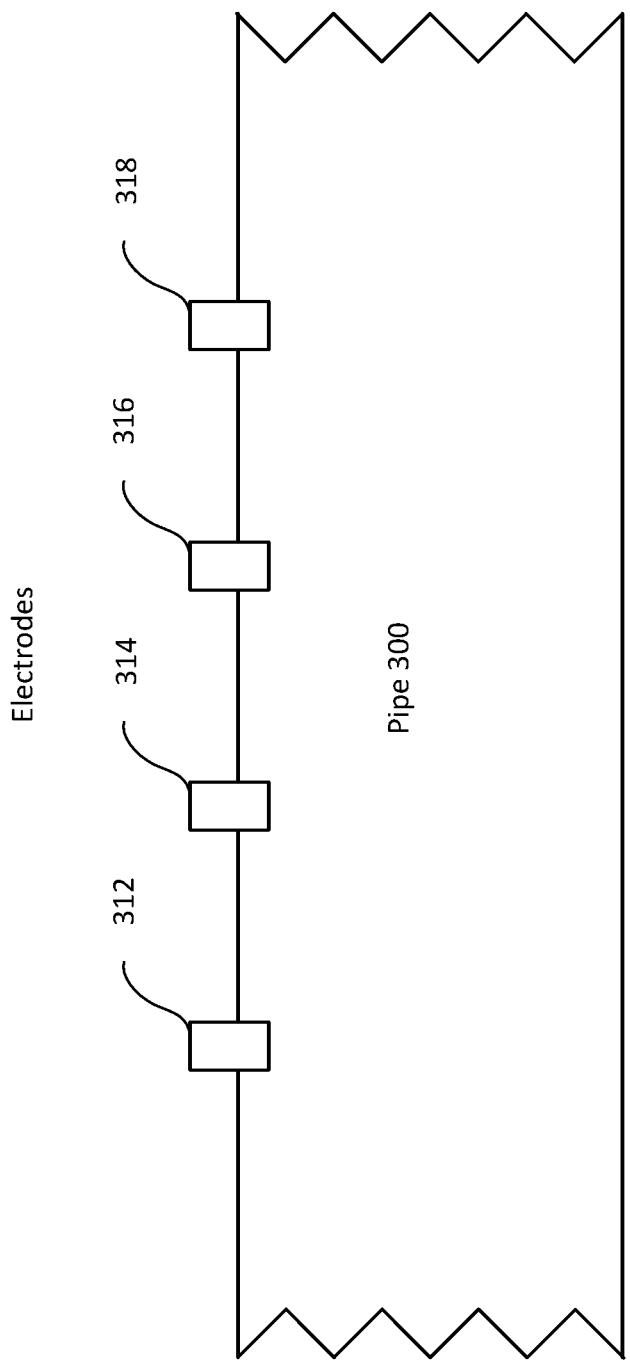
FIG. 3 illustrates an example placement of electrodes along a pipe.

Electrodes being positioned at different locations along the pipe may include the electrodes being positioned at different locations along the length of the pipe. Electrodes being positioned at different locations along the pipe may include the electrodes being positioned at different locations along the direction in which the pipe runs. For example, FIG. 3 illustrates an example placement of electrodes 312, 314, 316, 318 along a pipe 300. The pipe 300 may extend laterally, and FIG. 3 may show a side view of the pipe 300. The electrodes 312, 314, 316, 318 may be positioned at different locations along the lateral direction in which the pipe runs.

Figure 4:
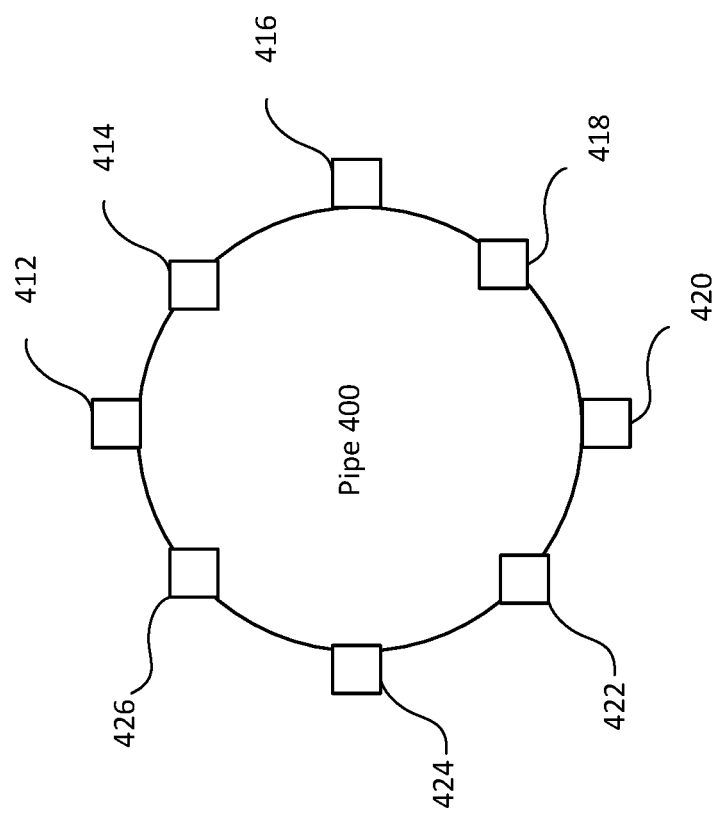
FIG. 4 illustrates an example placement of electrodes along a pipe.

Electrodes being positioned at different locations along the pipe may include the electrodes being positioned at different locations along the circumference of the pipe. Electrodes being positioned at different locations along the pipe may include the electrodes being positioned at different locations around a plane going through the pipe. For example, FIG. 4 illustrates an example placement of electrodes 412, 414, 416, 418, 420, 422, 424, 426 along a pipe 400. FIG. 4 may show a cross-sectional view of the pipe 400. The electrodes 412, 414, 416, 418, 420, 422, 424, 426 may be positioned at different locations along the circumference of the pipe 400. Other positionings of the electrodes are contemplated.

The set(s) of electrodes 14 may be configured to measure one or more impedance characteristics of the fluid inside the pipe. One or more electrodes of the set(s) of electrodes 14 may include and/or may be coupled to one or more impedance sensors (e.g., voltage sensors, current sensors) to perform the measurement of impedance characteristic(s) of the fluid inside the pipe. One or more electrodes of the set(s) of electrodes may include and/or may be coupled to the signal generator(s) 15 to induce voltage difference between different locations along the pipe. For example, one set of electrodes may include/be coupled to the impedance sensor(s) while another set of electrodes may include/be coupled to the signal generator(s) 15. As another example, same electrodes may include/be coupled to the impedance sensor(s) and the signal generator(s), and one or more circuitry/logic (e.g., multiplexer(s)) may be used to switch the function of the electrodes between measuring impedance characteristic(s) and inducing voltage difference.

The set(s) of electrodes 14 may be configured to measure impedance characteristic(s) of the fluid inside the pipe after voltage difference has been induced between different locations along the pipe (e.g., within the inner volume of the pipe, within the material of the pipe, on the inner surface of the pipe, on the outer surface of the pipe, and/or outside the pipe). The set(s) of electrodes 14 may measure impedance characteristics of the fluid inside the pipe by taking measurements from points within the inner volume of the pipe, within the material of the pipe, on the inner surface of the pipe, on the outer surface of the pipe, and/or outside the pipe. Measuring an impedance characteristic of the fluid inside the pipe may include ascertaining, accessing, checking, determining, estimating, examining, identifying, monitoring, observing, tracking, and/or otherwise measuring the impedance characteristic of the fluid inside the pipe. An impedance characteristic of the fluid inside the pipe may refer to a property, an attribute, a quality, a feature, a quantity, and/or other characteristic of the fluid relating to electrical impedance. Electrical impedance my include complex impedance, resistance, reactance (inductive reactance, capacitive reactance), and/or other impedance. For example, an impedance characteristic of the fluid inside the pipe measured by the set(s) of electrodes 14 may include current between different locations along the pipe (e.g., between different points within the inner volume of the pipe, within the material of the pipe, on the inner surface of the pipe, on the outer surface of the pipe, and/or outside the pipe). Alternatively or in addition, an impedance characteristic of the fluid inside the pipe measured by the set(s) of electrodes 14 may include voltage difference between different locations along the pipe (e.g., between different points within the inner volume of the pipe, within the material of the pipe, on the inner surface of the pipe, on the outer surface of the pipe, and/or outside the pipe).

For example, referring to FIG. 3, voltage difference may be induced between the location of the electrode 312 and the location of the electrode 318 (e.g., via applying voltage and/or current between the electrodes 312, 318). An impedance characteristic of the fluid inside the pipe 300 measured by a set of electrodes may include the current flowing between the location of the electrode 314 and the location of the electrode 316 and/or the voltage difference between the location of the electrode 314 and the location of the electrode 316 (measured using the electrodes 314, 316).

Referring to FIG. 4, voltage difference may be induced between the location of the electrode 412 and the location of the electrode 418 (e.g., via applying voltage and/or current between the electrodes 412, 418). An impedance characteristic of the fluid inside the pipe 400 measured by a set of electrodes may include the current flowing between the location of the electrode 414 and the location of the electrode 416 and/or the voltage difference between the location of the electrode 414 and the location of the electrode 416 (measured using the electrodes 414, 416).

In some implementations, impedance of the fluid inside the pipe may be determined based on the impedance characteristic(s) measured by the set(s) of electrodes 14. For example, impedance of the fluid inside the pipe may be determined based on current and/or voltage measured by the set(s) of electrodes 14, the current and/or voltage applied to induce the voltage difference, and/or other information. Other measurement of the impedance characteristic(s) of the fluid inside the pipe are contemplated.

The signal generator(s) 15 may be configured to generate one or more multi-frequency signals. The signal generator(s) 15 may include one or more electronic devices that generate one or more electronic signals. The signal generator(s) 15 may generate electronic signal(s) with set properties of amplitude, frequency, and/or wave shape. For example, the signal generator(s) 15 may include and/or be an AC source, and the AC source may be used to generate multi-frequency signal(s). A multi-frequency signal may refer to a signal having multiple frequencies. A multi-frequency signal may have multiple frequencies based on the frequency of the signal changing over time. For example, a multi-frequency signal may include a voltage chirp signal, a current chirp signal, and/or other chirp signal. The frequency of the chirp signal may change (e.g., increase, decrease) with time. For example, the frequency of a voltage chirp signal may change from 1 kHz to 50 kHz over a period of time (e.g., 10 ms). Use of other multi-frequency signals (e.g., Gaussian pulse, tone burst, linear chirps, nonlinear chirps, and other tailored excitations) are contemplated.

The multi-frequency signal(s) generated by the signal generator(s) 15 may induce voltage difference between different locations along the pipe (e.g., within the inner volume of the pipe, within the material of the pipe, on the inner surface of the pipe, on the outer surface of the pipe, and/or outside the pipe). The multi-frequency signal(s) generated by the signal generator(s) 15 may be applied to one or more electrodes to induce voltage across different portions of the pipe (e.g., within the inner volume of the pipe, within the material of the pipe, on the inner surface of the pipe, on the outer surface of the pipe, and/or outside the pipe). For example, referring to FIG. 3, the multi-frequency signal(s) may be applied to the electrodes 312, 318 to induce voltage difference between locations of the electrodes 312, 318. Referring to FIG. 4, the multi-frequency signal(s) may be applied to the electrodes 412, 418 to induce voltage difference between locations of the electrodes 412, 418.

The voltage difference between different locations along the pipe may be induced for multi-frequency measurement of the impedance characteristic(s) of the fluid inside the pipe. The voltage difference induced using the multi-frequency signal(s) may be used to measure impedance characteristic(s) across over a range of frequencies. The multi-frequency signal(s) may cause multi-frequency voltage difference between different locations along the pipe, which may be measured using the set(s) of electrodes 14. The multi-frequency measurement of the impedance characteristic(s) of the fluid inside the pipe may be used to characterize fluid flow dynamics that are not possible with low frequency signals. The multi-frequency measurement of the impedance characteristic(s) of the fluid inside the pipe may provide richer set of information than performing impedance characteristic measurement at a single frequency or no frequency (using DC signal).

The impedance characteristic(s) of the fluid inside the pipe may change based on the characteristic(s) of the fluid inside the pipe. For example, the impedance characteristic(s) of the fluid inside the pipe may change based on the composition of the fluid inside the pipe (e.g., oil-water concentration in the fluid, number and/or sizes of bubbles inside the fluid). Additionally, the impedance characteristic(s) of the fluid inside the pipe may change based on the frequency of the signal used to induce the voltage difference.

Figure 5:
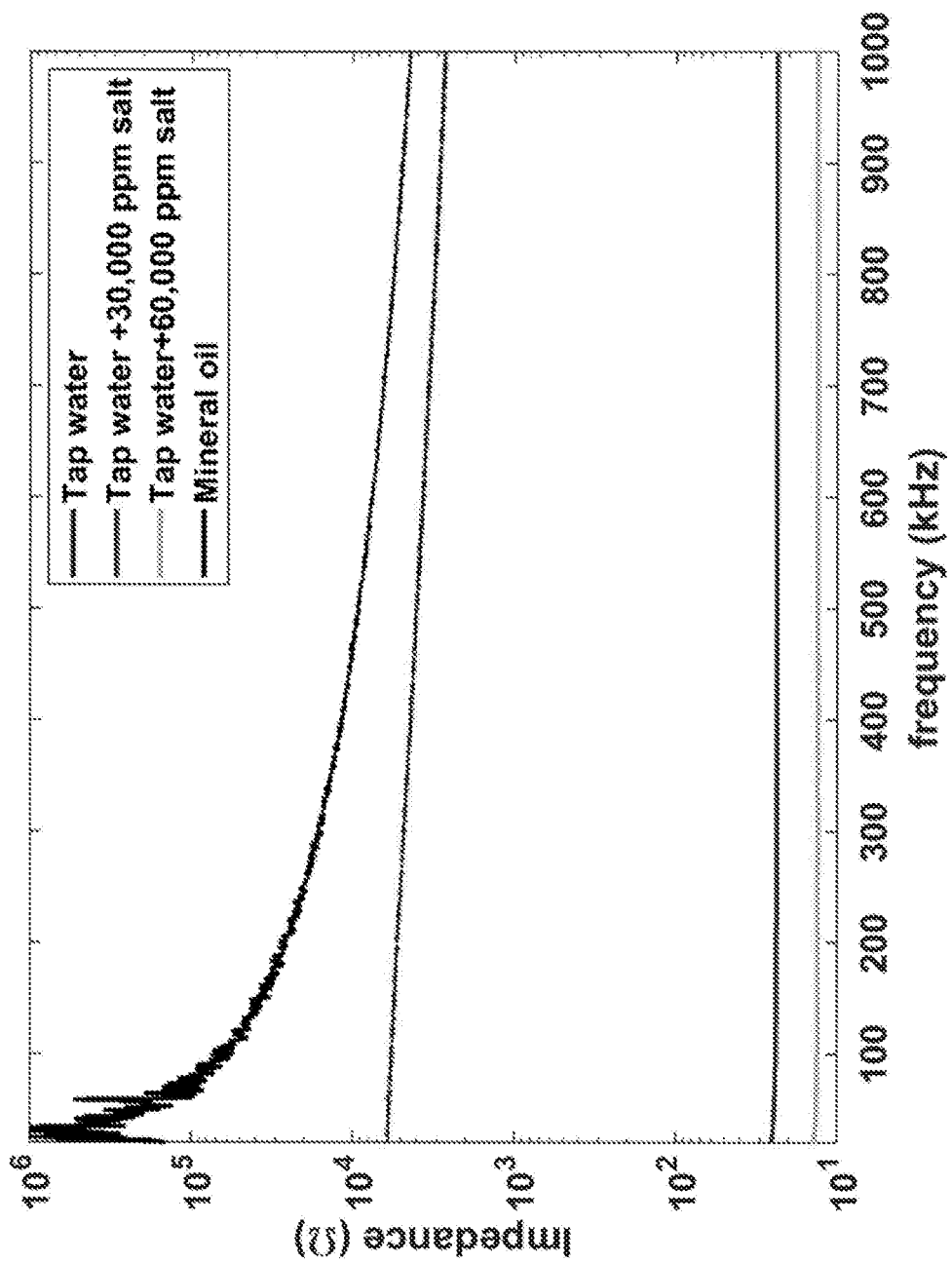
FIG. 5 illustrates example frequency-dependent impedance characteristic of fluid.

For example, FIG. 5 illustrates example frequency-dependent impedance characteristic of fluid. FIG. 5 shows electrical impedance curves (log-scale on y-axis) for mineral oil and tap water with different salt concentrations (30,000 and 60,000 ppm). As seen in FIG. 5, different impedance is measured for different fluid compositions. For instance, much higher impedance is measured for mineral oil than for tap water. As salt concentration in the fluid increases, the impedance reduces (due to the fluid becoming more conductive with increasing salt concentration). Additionally, the impedance curve becomes flatter with higher frequency as the salt concentration increases, an indication that the fluid may tend to be purely resistive in nature as opposed to being capacitive/inductive.

Thus, multi-frequency measurement of the impedance characteristic(s) enables characterization of frequency-dependent subsurface electrical impedance that is in general sensitive to fluid composition (e.g., hydrocarbon, fracking fluid). The multi-frequency measurement of the impedance characteristic(s) (e.g., as defined within multi-frequency impedance maps) may be analyzed to determine the composition of fluid in different parts of the well, which may enable enhanced detectability of hydrocarbon production zones in wells. The multi-frequency measurement of the impedance characteristic(s) may be used to monitor changes in composition of the fluid. For example, the multi-frequency measurement of the impedance characteristic(s) may be used to monitor subsurface electrical impedance that changes with the ratio of hydrocarbon-to-water in the fluid (e.g., oil-to-water concentration), which may be used to determine time-varying spatial distribution of hydrocarbon/water across different stages of a well. The time-varying spatial distribution of hydrocarbon/water across the stages may be used to quantify the net hydrocarbon flow in the well.

Referring back to FIG. 1, the electronic storage 13 may be configured to include electronic storage medium that electronically stores information. The electronic storage 13 may store software algorithms, information determined by the processor 11, information received remotely, and/or other information that enables the system 10 to function properly. For example, the electronic storage 13 may store information relating to electrode, information relating to impedance characteristic, information relating to fluid, information relating to pipe, information relating to signal generator, information relating to multi-frequency signal, information relating to multi-frequency measurement of impedance characteristic, and/or other information.

The processor 11 may be configured to provide information processing capabilities in the system 10. As such, the processor 11 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. The processor 11 may be configured to execute one or more machine-readable instructions 100 to facilitate determining fluid characteristics. The machine-readable instructions 100 may include one or more computer program components. The machine-readable instructions 100 may include one or more of a measurement component 102, a characteristic component 104, and/or other computer program components.

The measurement component 102 may be configured to obtain the multi-frequency measurement of the impedance characteristic(s) of the fluid inside the pipe. Obtaining multi-frequency measurement of impedance characteristic(s) may include one or more of accessing, acquiring, analyzing, creating, determining, examining, generating, identifying, loading, locating, opening, receiving, retrieving, reviewing, selecting, storing, utilizing, and/or otherwise obtaining the multi-frequency measurement of the impedance characteristic(s). The measurement component 102 may obtain the multi-frequency measurement of the impedance characteristic(s) of the fluid inside the pipe from one or more locations. For example, the multi-frequency measurement of the impedance characteristic(s) of the fluid inside the pipe may be obtained from the set(s) of electrodes 14 and/or other locations. The multi-frequency measurement of the impedance characteristic(s) of the fluid inside the pipe may be obtained directly and/or indirectly from the set(s) of electrodes 14.

The values of the impedance characteristic(s) of the fluid measured by the set(s) of electrodes 14 may depend on and/or be indicative of the composition of fluid inside the pipe. For example, the values of the impedance characteristic(s) of the fluid measured by the set(s) of electrodes 14 may depend on and/or be indicative of the oil/water concentration in the fluid.

Figure 6:
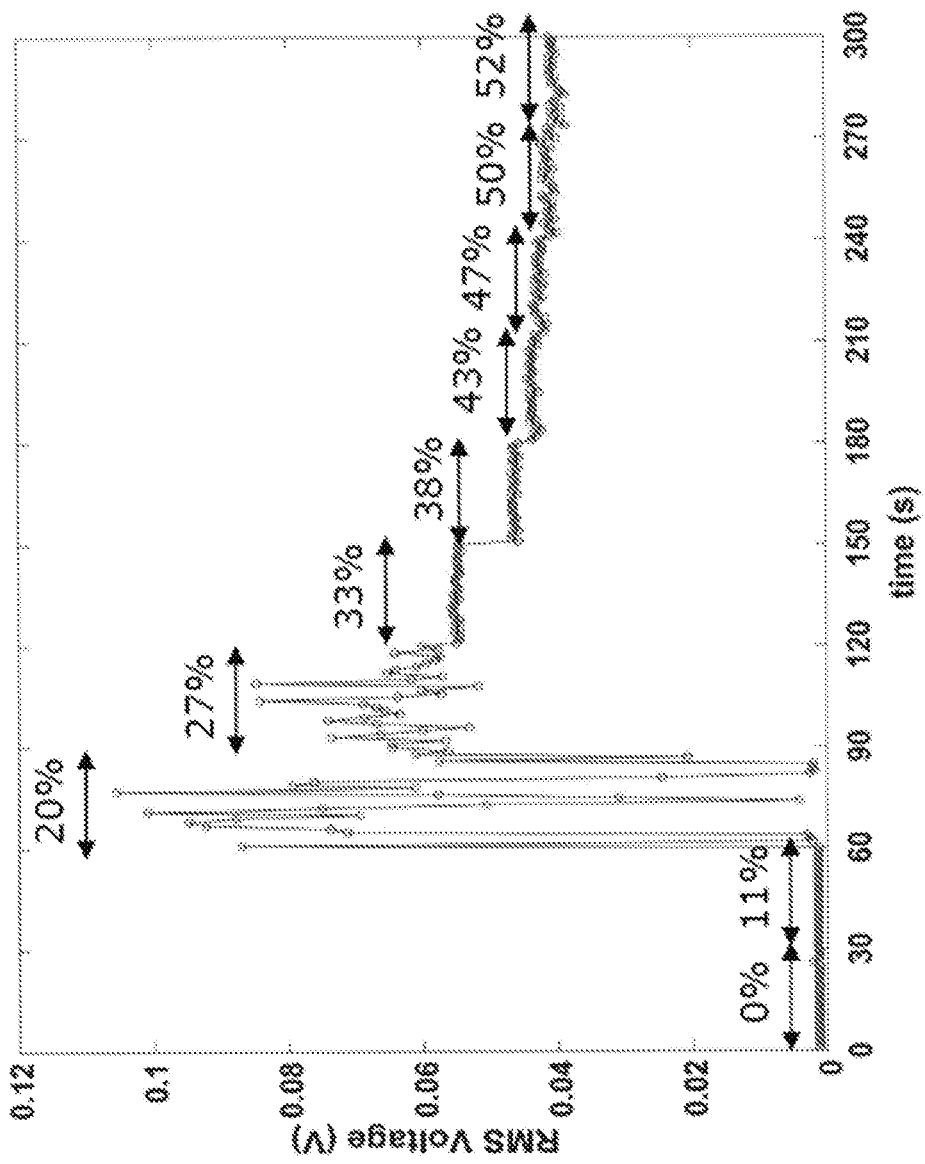
FIG. 6 illustrates example voltages measured for fluid with different water/oil composition.

FIG. 6 illustrates example voltages measured for fluid with different water/oil composition. FIG. 6 shows measured RMS voltage for fluid with different concentration of water and oil. The fluid may start with pure oil concentration (no water), and salt water (referred to as water herein) may be added to the fluid so that the percentage of water in the fluid increases (0%, 11%, 20%, 27%, 33%, 38%, 43%, 47%, 50%, and 52%). A voltage chirp signal (1 kHz to 50 kHz) may be applied to induce voltage difference. When the fluid composition is close to pure oil, RMS voltage is close to zero, indicating that no conducting path is present in the fluid for current flow. When the fluid composition is between 20-27% water (80-73% oil), large fluctuations are observed in the measured RMS voltage. This may be indicative of conductive pathways being formed in the fluid, with the pathways dynamically breaking due to the low concentration of water. From such measurements, heterogenous oil-water composition may be differentiated and flow dynamic information may be extracted. With further increase in water concentration, conducting paths are established and the fluid conductivity gradually increases. This results in a step-like decrease of the measured RMS voltage that levels-off at when the fluid composition reaches 50% water-50% oil. Thus, the sensitivity of the fluid-composition determination from the voltage-input-voltage-output measurement shown in FIG. 6 may range between 0% water-100% oil to about 50% water-50% oil. With greater concentration of water, the measured RMS voltage may lose sensitivity.

Figure 7:
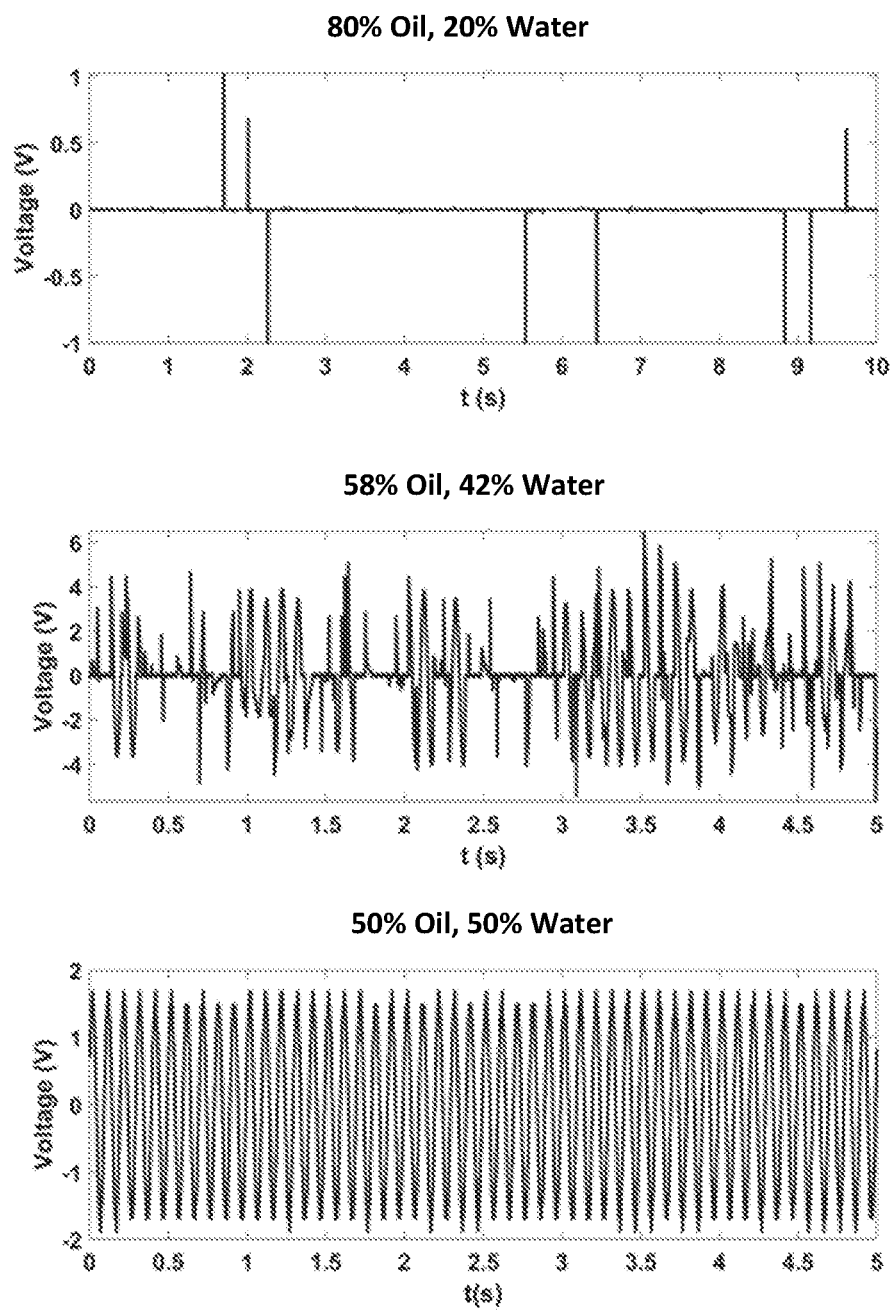
FIG. 7 illustrates example voltages measured for fluid with different water/oil composition.

FIG. 7 illustrates example voltages measured for fluid with different water/oil composition. FIG. 7 shows measured voltage for fluid with different concentration of water and oil. A 10 Hz sine-wave excitation signal may be applied to induce voltage difference. When the fluid has high oil concentration (e.g., 80% oil), only a few conducting paths may be formed and may be dynamically broken, resulting in the occasional spikes in the measured voltage signal. With increase in water concentration, more conducting paths are formed. With 58% oil, the measured voltage signal indicates more conducting paths existing within the fluid for larger extent of time. With 50% oil concentration, the measured voltage signals indicate that conducting paths exist within the fluid for all time (e.g., the fluid is completely conducting). Such measurements may be used to estimate oil concentration in the fluid and/to track dynamics of fluid flow in the pipe.

Figure 8:
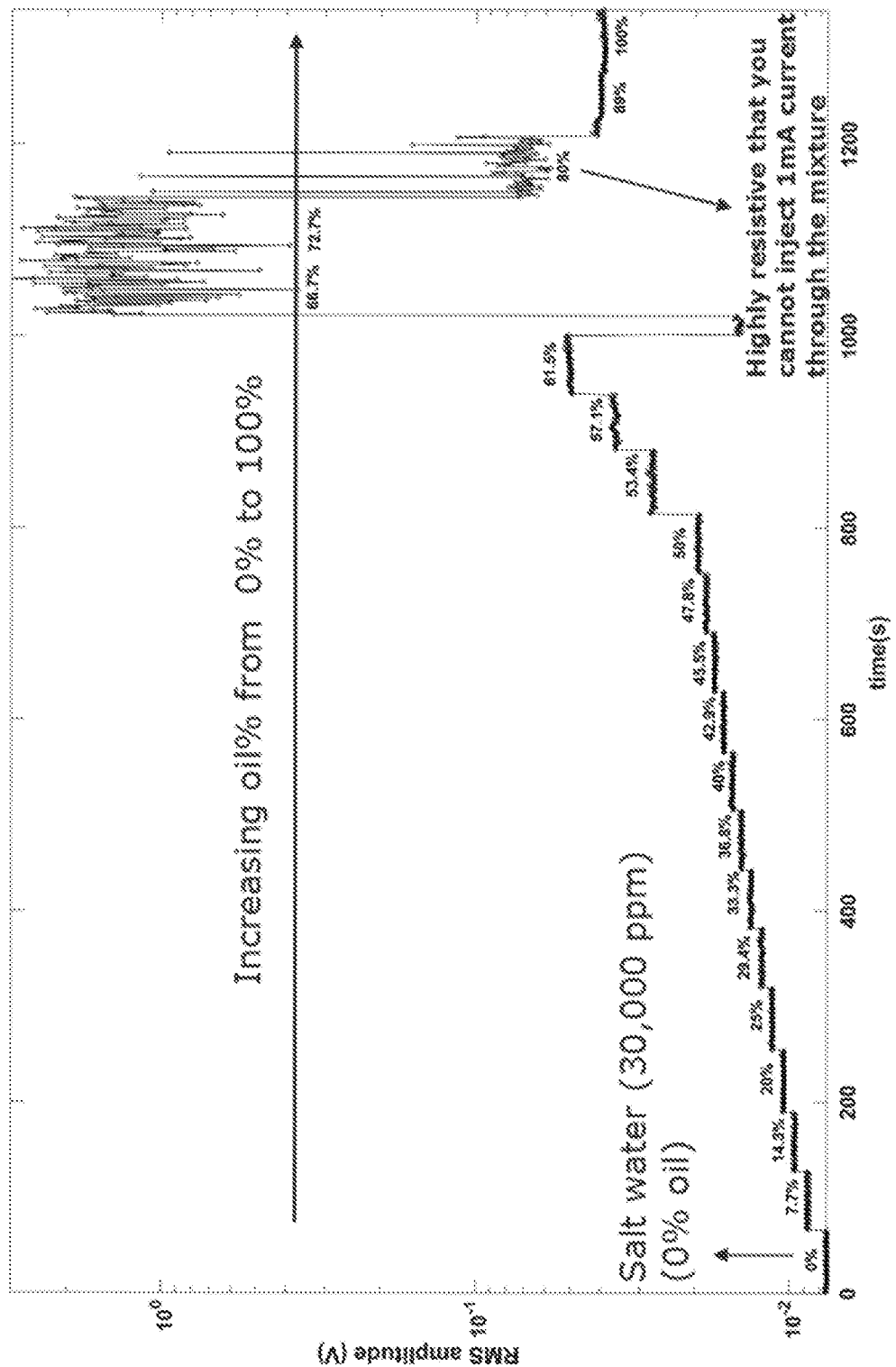
FIG. 8 illustrates example voltages measured for fluid with different water/oil composition.

FIG. 8 illustrates example voltages measured for fluid with different water/oil composition. FIG. 8 shows measured RMS voltage for fluid with different concentration of water and oil. The fluid may start with pure salt water concentration (no oil), and oil may be added to the fluid so that the percentage of oil in the fluid increases (0%, 7.7%, 14.3%, 20%, 25%, 29.4%, 33.3%, 36.8%, 40%, 42.9%, 45.5%, 47.8%, 50%, 53.4%, 57.1%, 61.5%, 66.7%, 72.7%, 80%, 89%, and 100%). A current chirp signal with amplitude of 1 mA may be applied to induce voltage difference. When the fluid composition is pure water, RMS voltage is close to zero. With increase in oil concentration, fluid conductivity gradually decreases. This results in a step-like increase of the measured RMS voltage that fluctuates when the fluid composition reaches around 65-70% oil. When the fluid composition reaches 80% oil, the fluid becomes highly resistive such that the 1 mA current cannot be injected through the fluid. The fluid may allow only allow a small part of the current to pass through and rest of the current may be reflected to the source of the current. Thus, the sensitivity of the fluid-composition determination from the current-input-voltage-output measurement shown in FIG. 8 may range between 100% water-0% oil to about 35% water-65% oil. With greater concentration of oil, the measured RMS voltage may lose sensitivity.

The characteristic component 104 may be configured to determine one or more characteristics of the fluid inside the pipe. A characteristic of the fluid inside the pipe may refer to a property, an attribute, a quality, a feature, a quantity, and/or other characteristic of the fluid inside the pipe. A characteristic of the fluid inside the pipe determined by the characteristic component 104 may refer to characteristic of the fluid at one or more locations inside the pipe. A characteristic of the fluid inside the pipe determined by the characteristic component 104 may refer to characteristic of the fluid at one or more moments (e.g., point(s) of time, duration(s) of time). A characteristic of the fluid inside the pipe may refer to a static characteristic and/or a dynamic characteristic of the fluid inside the pipe.

For example, a characteristic of the fluid inside the pipe determined based on the multi-frequency measurement of the impedance characteristic(s) of the fluid inside the pipe may refer to fluid composition, fluid flow regime, and/or other characteristic of the fluid inside the pipe. The fluid composition may refer to what materials are included in the fluid and/or concentration of materials in the fluid, such as percentage of oil, water, and/or other composition in the fluid. The fluid flow regime may refer to fluid structure and/or distribution of composition in the fluid. For example, fluid flow regime may include stratified flow (fluid separated into different layers, with light fluids flowing above heavier fluids), bubbly flow (small bubbles dispersed or suspended in liquid continuum), slug flow (intermittent sequence of liquid slugs followed by longer gas bubbles flowing through the pipe), and/or other types of flow. In some implementations, dynamics of the impedance characteristic measurement may be used to identify and/or differentiate fluid composition and/or fluid flow regime. For example, high concentration of oil in the fluid may result in steady voltage reading, while bubbly flow may result in fluctuation in the voltage reading. Measurements performed at different locations along the pipe may be used to track movement of fluid (e.g., movement of bubbles) through the pipe. Determination of other characteristics of fluid is contemplated.

The characteristic(s) of the fluid inside the pipe may be determined based on the multi-frequency measurement of the impedance characteristic(s) of the fluid inside the pipe and/or other information. Determination of a characteristic of the fluid inside the pipe may include identification of the characteristic, quantification of the characteristic, and/or other determination of the characteristic. For example, determination of a characteristic of the fluid inside the pipe may include identification of what materials are included in/make up the fluid, the concentration of material in the fluid, and/or distribution of material in the fluid.

One or more inversion techniques may be used to determine the characteristic(s) of the fluid inside the pipe based on the multi-frequency measurement of the impedance characteristic(s) of the fluid inside the pipe. For example, based on the measured values of the impedance characteristic(s) of the fluid inside the pipe, the fluid composition and/or the fluid flow regime of the fluid inside the pipe may be determined. In some implementations, the characteristic(s) of the fluid inside the pipe may be determined directly from the measured values of the impedance characteristic(s) of the fluid. For example, the fluid composition and/or the fluid flow regime of the fluid inside the pipe may be determined based on voltage readings and/or current readings from the set(s) of electrodes 14. In some implementations, the characteristic(s) of the fluid inside the pipe may be determined indirectly from the measured values of the impedance characteristic(s) of the fluid. For example, voltage readings and/or current readings from the set(s) of electrodes 14 may be used to calculate the impedance of the fluid inside the pipe, and the fluid composition and/or the fluid flow regime of the fluid inside the pipe may be determined based on the calculated impedance.

For example, referring to FIG. 3, the composition of fluid inside the lateral middle of the pipe 300 may be determined based on the multi-frequency measurement of the impedance characteristic(s) of the fluid measured using the electrodes 314, 316. The composition of the fluid to the left may be determined based on the multi-frequency measurement of the impedance characteristic(s) of the fluid measured using the electrodes 312, 314. The composition of the fluid to the right may be determined based on the multi-frequency measurement of the impedance characteristic(s) of the fluid measured using the electrodes 314, 316. The measured values of the impedance characteristic(s) of the fluid from the electrodes 312, 314, 316, 318 may be used to determine the composition of the fluid between/below pairs of the electrodes 312, 314, 316, 318.

Referring to FIG. 4, the flow regime of the fluid inside the pipe 400 may be determined based on the multi-frequency measurement of the impedance characteristic(s) of the fluid measured using the electrodes 412, 414, 416, 418, 420, 422, 424, 426. The values of the impedance characteristic(s) of the fluid measured near/on the circumference of the pipe 400 may be used to determine the distribution of materials in the fluid inside the pipe 400.

In some implementations, experimental data and/or modeling data may be used to determine the characteristic(s) of the fluid inside the pipe from the multi-frequency measurement of the impedance characteristic(s) of the fluid inside the pipe. The multi-frequency measurement of the impedance characteristic(s) of the fluid inside the pipe may be interpreted and/or analyzed using the experimental data and/or modeling data to determine the characteristic(s) of the fluid inside the pipe. Experimental data may refer to data obtained from one or more experiments. For example, experiments may be performed to measure impedance characteristic(s) of the fluid inside the pipe for different fluid compositions and/or different fluid flow regimes. The multi-frequency impedance measurements from the experiments may be used to interpret and/or analyze the multi-frequency impedance measurements for a particular pipe/fluid inside the pipe. For example, field measurements from a pipe/fluid inside the pipe may be matched/compared to the measurements from the experiment(s) to determine the characteristic(s) of the fluid inside the pipe.

Modeling data may refer to data obtained from one or more modeling techniques (e.g., finite element methods) of fluid inside a pipe. Modeling may include computational/numerical model of the pipe and the fluid inside the pipe. For example, modeling may be performed to simulate flow of different fluid through different pipes. Modeling may be performed for different types of fluid, different types of flow, and/or different types of pipes (e.g., different pipe shape, different pipe length, different pipe material). Modeling may simulate the multi-frequency measurement of the impedance characteristic(s) of the fluid inside the pipe. Modeling may also simulate the values of the impedance characteristic(s) of the fluid that would be measured for different types of pipes, different types of fluid, and/or different types of flow. The multi-frequency impedance measurements simulated through modeling may be used to interpret and/or analyze the multi-frequency impedance measurements for a particular pipe/fluid inside the pipe. For example, field measurements from a pipe/fluid inside the pipe may be matched/compared to the simulated measurements from modeling to determine the characteristic(s) of the fluid inside the pipe.

Figure 10:
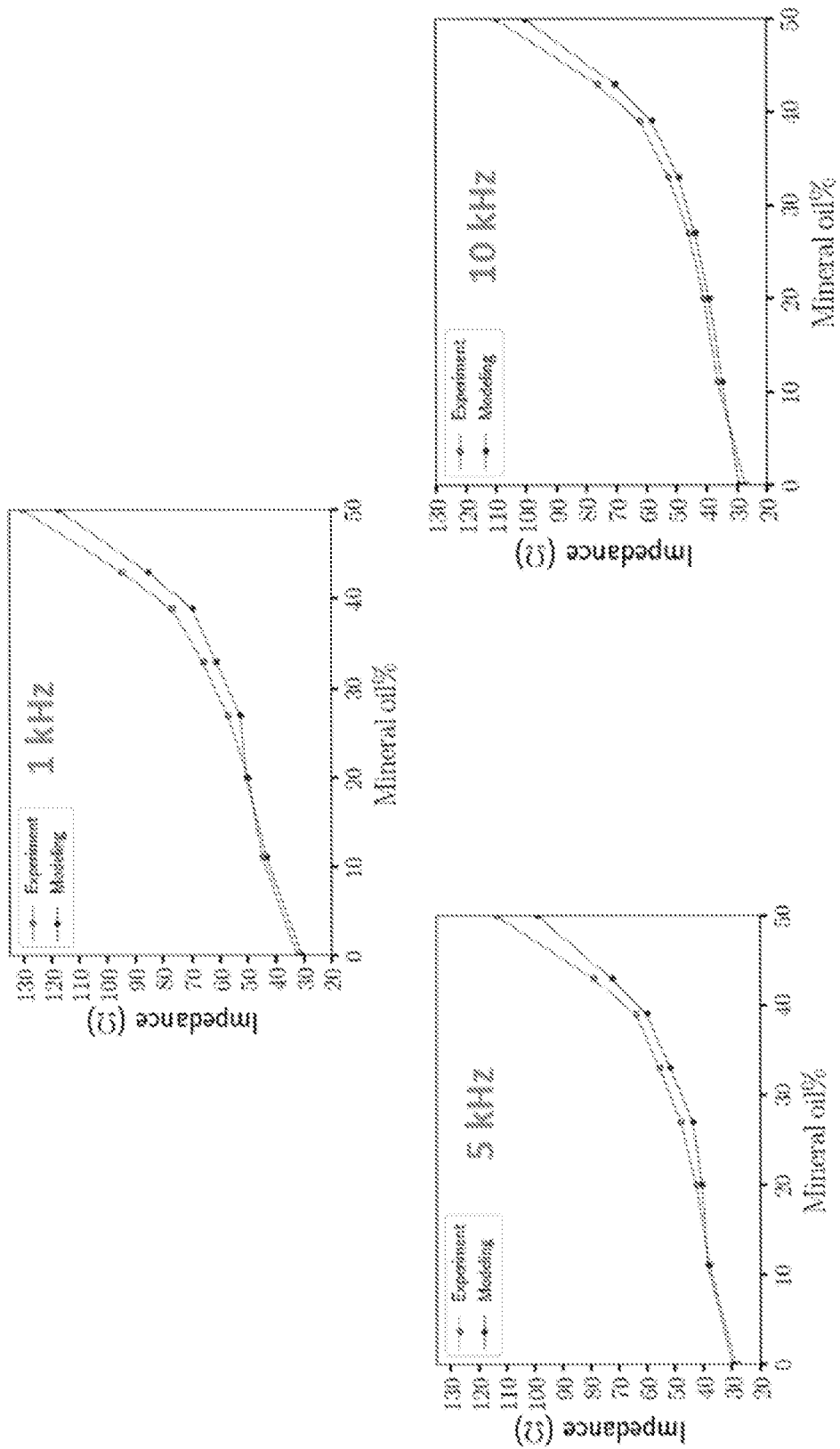
FIG. 10 illustrates example comparisons of experimental measurements of fluid impedance and simulated measurements of fluid impedance.

FIG. 10 illustrates example comparisons of experimental measurements of fluid impedance and simulated measurements of fluid impedance. The experimental measurements and the simulated measurements may be performed using frequencies of 1 kHz, 5 kHz, and 10 kHz. The impedance plots from experiments agree with impedance plots from modeling at multiple frequencies, indicating that multi-frequency impedance measurements simulated through modeling may be used to interpret and/or analyze the multi-frequency impedance measurements made in the real world.

In some implementations, different types of multi-frequency signal may be generated/applied to induce voltage for multi-frequency impedance measurement. For example, applying a voltage signal to induce the voltage difference may result in the multi-frequency impedance measurement being sensitive for fluid composition from 0% water -100% oil to about 50% water-50% oil, while applying a current signal to induce the voltage difference may result in the multi-frequency impedance measurement being sensitive for fluid composition from 35% water-65% oil to about 100% water-0% oil. Whether a voltage signal or a current signal is used for the multi-frequency impedance measurement may depend on the (estimated) concentration inside the fluid. For example, the voltage signal may be used for oil-rich fluid while the current signal may be used for water-rich fluid. In some implementations, the signal used for multi-frequency impedance measurement may switch from one mode (e.g., voltage signal) to another mode (e.g., current signal).

Figure 9A:
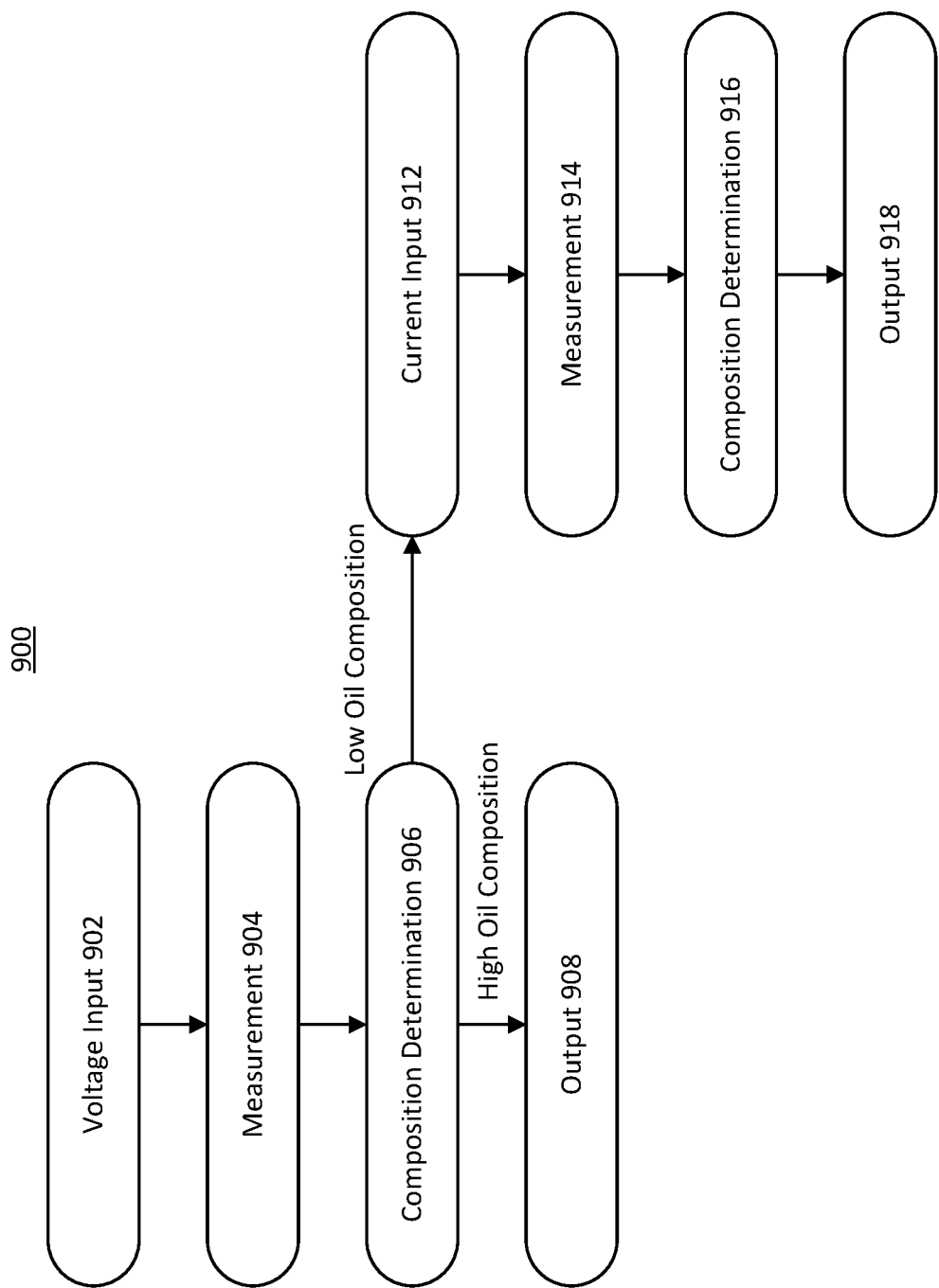
FIG. 9A illustrates an example process for determining composition of fluid inside a pipe.

FIG. 9A illustrates an example process 900 for determining composition of fluid inside a pipe. The process 900 may begin with voltage input 902, where a voltage signal is used to induce voltage difference inside a pipe/fluid inside the pipe. Measurement 904 may include multi-frequency measurement of the impedance characteristic(s) of the fluid. Composition determination 906 may be performed to determine concentration of materials inside the fluid, such as concentration of oil inside the fluid. Based on the concentration of the oil being high (e.g., greater than 50%), the concentration of the materials/measurement may be output 908.

Based on the concentration of the oil being low (e.g., less than 50%), the mode of excitation may switch to current input 912, where a current signal may be used to induce voltage difference inside the pipe/fluid inside the pipe. Measurement 914 may include multi-frequency measurement of the impedance characteristic(s) of the fluid. Composition determination 916 may be performed to determine concentration of materials inside the fluid. The concentration of the materials/measurement may be output 918.

Figure 9B:
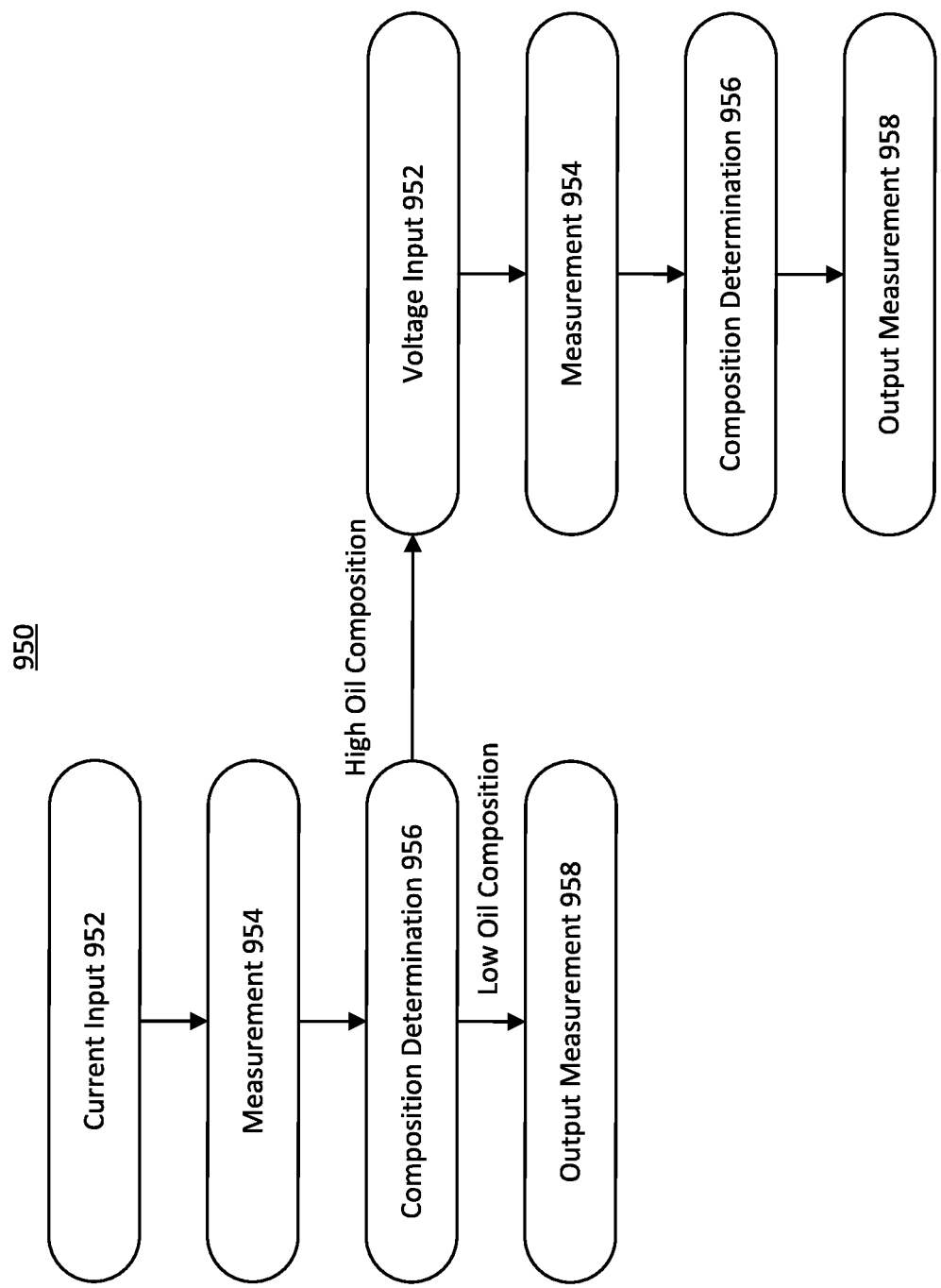
FIG. 9B illustrates an example process for determining composition of fluid inside a pipe.

FIG. 9B illustrates an example process 950 for determining composition of fluid inside a pipe. The process 950 may begin with current input 952, where a current signal is used to induce voltage difference inside a pipe/fluid inside the pipe. Measurement 954 may include multi-frequency measurement of the impedance characteristic(s) of the fluid. Composition determination 956 may be performed to determine concentration of materials inside the fluid, such as concentration of oil inside the fluid. Based on the concentration of the oil being low (e.g., less than 50%), the concentration of the materials/measurement may be output 958.

Based on the concentration of the oil being high (e.g., greater than 50%), the mode of excitation may switch to voltage input 952, where a voltage signal may be used to induce voltage difference inside the pipe/fluid inside the pipe. Measurement 954 may include multi-frequency measurement of the impedance characteristic(s) of the fluid. Composition determination 956 may be performed to determine concentration of materials inside the fluid. The concentration of the materials/measurement may be output 958. Usage of other concentration(s) of oil to switch between input voltage signal and input current signal are contemplated.

In some implementations, the characteristic(s) of the fluid inside the pipe determined for different times may be used to determine one or more dynamic characteristics of the fluid inside the pipe. For example, multi-frequency impedance measurement taken for different times at a particular location along the pipe may be used to determine how the fluid flowing through the pipe is changing over time. For instance, multi-frequency impedance measurement taken for different times at a particular location along the pipe may be used to determine changes in fluid composition and/or fluid flow regime over time.

In some implementations, the characteristic(s) of the fluid inside the pipe determined for different locations may be used to determine one or more dynamic characteristics of the fluid inside the pipe. For example, multi-frequency impedance measurements taken at different times for different locations along the pipe may be used to determine how the fluid is flowing through the pipe. For instance, multi-frequency impedance measurement taken at different times for different locations along the pipe may be used to track movement of particular fluid flow regime (e.g., stratified flow, bubbly flow, slug flow) through the pipe.

In some implementations, the pipe may be inside a horizontal well, and the characteristic(s) of the fluid inside the pipe determined for different locations may be used to identify producing stages and non-producing stages inside the horizontal well. For example, the horizontal well may include multiple stages, and different sets of electrodes may be positioned at/near individual stages. The multi-frequency impedance measurement taken at/for the individual stages may be used to determine oil concentration at/near the individual stages, which may then be used to determine whether the individual stages are producing oil and/or the extent to which the individual stages are producing oil. The multi-frequency impedance measurement taken at/for the individual stages may be used to determine distributed hydrocarbon flow along the horizontal well. Thus, the disclosure herein may provide a nonintrusive, remote monitoring technique for evaluating horizontal well efficiency (e.g., hydraulic fracturing efficiency). The multi-frequency impedance measurement taken at/for the individual stages may be used to interrogate the horizontal and generate subsurface electrical (frequency-dependent conductivity) maps that enables production zone localization. Such information may be used to determine well placements, improve fracturing treatments, identify water influx, and/or otherwise facilitate operation of wells.

Implementations of the disclosure may be made in hardware, firmware, software, or any suitable combination thereof. Aspects of the disclosure illustrated in FIG. 1 may be implemented as instructions stored on a machine-readable medium, which may be read and executed by one or more processors. A machine-readable medium may include any mechanism for storing or transmitting information in a form readable by a machine (e.g., a computing device). For example, a tangible (non-transitory) machine-readable storage medium may include read-only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

In some implementations, some or all of the functionalities attributed herein to the system 10 in FIG. 1 may be provided by external resources not included in the system 10. External resources may include hosts/sources of information, computing, and/or processing and/or other providers of information, computing, and/or processing outside of the system 10.

Although the processor 11, the electronic storage 13, the set(s) of electrodes 14, and the signal generator(s) 15 are shown to be connected to the interface 12 in FIG. 1, any communication medium may be used to facilitate direct and/or indirect interaction between any components of the system 10. One or more components of the system 10 may communicate with each other through hard-wired communication, wireless communication, or both. For example, one or more components of the system 10 may communicate with each other through a network. For example, the processor 11 may wirelessly communicate with the electronic storage 13. By way of non-limiting example, wireless communication may include one or more of radio communication, Bluetooth communication, Wi-Fi communication, cellular communication, infrared communication, or other wireless communication. Other types of communications are contemplated by the present disclosure.

Although the processor 11 is shown in FIG. 1 as a single entity, this is for illustrative purposes only. In some implementations, the processor 11 may comprise a plurality of processing units. These processing units may be physically located within the same device, or the processor 11 may represent processing functionality of a plurality of devices operating in coordination. The processor 11 may be separate from and/or be part of one or more components of the system 10. The processor 11 may be configured to execute one or more components by software; hardware; firmware; some combination of software, hardware, and/or firmware; and/or other mechanisms for configuring processing capabilities on the processor 11.

It should be appreciated that although computer program components are illustrated in FIG. 1 as being co-located within a single processing unit, in implementations in which processor 11 comprises multiple processing units, one or more of computer program components may be located remotely from the other computer program components. While computer program components are described as performing or being configured to perform operations, computer program components may comprise instructions which may program processor 11 and/or system 10 to perform the operation.

While computer program components are described herein as being implemented via processor 11 through machine-readable instructions 100, this is merely for ease of reference and is not meant to be limiting. In some implementations, one or more functions of computer program components described herein may be implemented via hardware (e.g., dedicated chip, field-programmable gate array) rather than software. One or more functions of computer program components described herein may be software-implemented, hardware-implemented, or software and hardware-implemented The description of the functionality provided by the different computer program components described herein is for illustrative purposes, and is not intended to be limiting, as any of computer program components may provide more or less functionality than is described. For example, one or more of computer program components may be eliminated, and some or all of its functionality may be provided by other computer program components. As another example, processor 11 may be configured to execute one or more additional computer program components that may perform some or all of the functionality attributed to one or more of computer program components described herein.

The electronic storage media of the electronic storage 13 may be provided integrally (i.e., substantially non-removable) with one or more components of the system 10 and/or as removable storage that is connectable to one or more components of the system 10 via, for example, a port (e.g., a USB port, a Firewire port, etc.) or a drive (e.g., a disk drive, etc.). The electronic storage 13 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. The electronic storage 13 may be a separate component within the system 10, or the electronic storage 13 may be provided integrally with one or more other components of the system 10 (e.g., the processor 11). Although the electronic storage 13 is shown in FIG. 1 as a single entity, this is for illustrative purposes only. In some implementations, the electronic storage 13 may comprise a plurality of storage units. These storage units may be physically located within the same device, or the electronic storage 13 may represent storage functionality of a plurality of devices operating in coordination.

Figure 2:
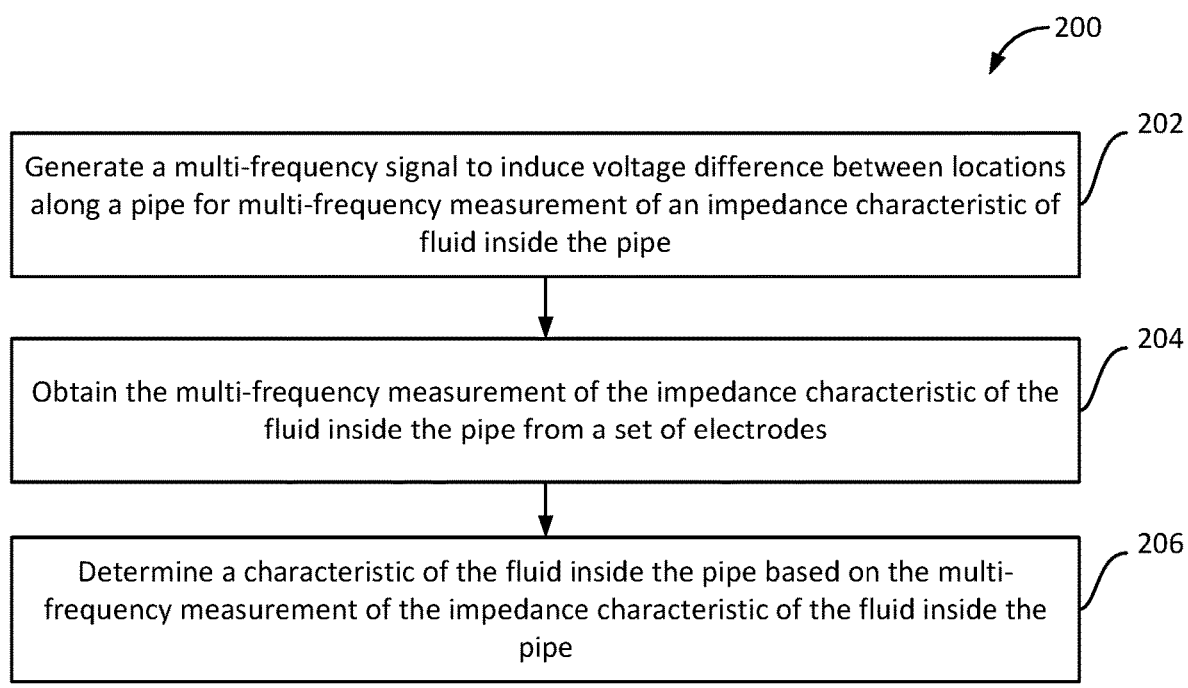
FIG. 2 illustrates an example method for determining fluid characteristics.

FIG. 2 illustrates method 200 for determining fluid characteristics. The operations of method 200 presented below are intended to be illustrative. In some implementations, method 200 may be accomplished with one or more additional operations not described, and/or without one or more of the operations discussed. In some implementations, two or more of the operations may occur substantially simultaneously.

In some implementations, one or more operations of the method 200 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operations of method 200 in response to instructions stored electronically on one or more electronic storage media. The one or more processing devices may include one or more devices configured through hardware, firmware, and/or software to be specifically designed for execution of one or more of the operations of method 200.

Referring to FIG. 2 and method 200, at operation 202, a multi-frequency signal may be generated to induce voltage difference between different locations along a pipe. The voltage different may be induced between a first location along the pipe and a second location along the pipe. The voltage difference may be induced for multi-frequency measurement of an impedance characteristic of the fluid inside the pipe. In some implementation, operation 202 may be performed by a component the same as or similar to the signal generator(s) 15 (Shown in FIG. 1 and described herein).

At operation 204, the multi-frequency measurement of the impedance characteristic of the fluid inside the pipe may be obtained from a set of electrodes. The set of electrodes may be configured to measure the impedance characteristic of fluid inside the pipe. The set of electrodes may include a first electrode positioned at the first location along the pipe, and a second electrode positioned at the second location along the pipe. In some implementation, operation 204 may be performed by a component the same as or similar to the measurement component 102 (Shown in FIG. 1 and described herein).

At operation 206, a characteristic of the fluid inside the pipe may be determined based on the multi-frequency measurement of the impedance characteristic of the fluid inside the pipe and/or other information. In some implementation, operation 206 may be performed by a component the same as or similar to the characteristic component 104 (Shown in FIG. 1 and described herein).

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system for determining fluid characteristics, the system comprising:
   a set of electrodes configured to measure an impedance characteristic of fluid inside a pipe, the set of electrodes including a first electrode positioned at a first location along the pipe and a second electrode positioned at a second location along the pipe;
   a signal generator configured to generate a multi-frequency signal, the multi-frequency signal inducing voltage difference between the first location along the pipe and the second location along the pipe, the voltage difference induced for multi-frequency measurement of the impedance characteristic of the fluid inside the pipe; and
   one or more physical processors configured by machine-readable instructions to:
      obtain the multi-frequency measurement of the impedance characteristic of the fluid inside the pipe from the set of electrodes; and
      determine fluid composition of the fluid inside the pipe based on the multi-frequency measurement of the impedance characteristic of the fluid inside the pipe, the fluid composition of the fluid including hydrocarbon concentration in the fluid;
   wherein:
      responsive to the voltage difference being initially induced for the multi-frequency measurement of the impedance characteristics of the fluid using voltage input and the hydrocarbon concentration in the fluid being lower than a first threshold value, the inducement of the voltage difference is switched from using the voltage input to using current input; and responsive to the voltage difference being initially induced for the multi-frequency measurement of the impedance characteristics of the fluid using the current input and the hydrocarbon concentration in the fluid being higher than a second threshold value, the inducement of the voltage difference is switched from using the current input to using the voltage input.

2. The system of claim 1, wherein the multi-frequency signal includes a voltage chirp signal.

3. The system of claim 1, wherein the multi-frequency signal includes a current chirp signal.

4. The system of claim 1, wherein the impedance characteristic of the fluid inside the pipe measured by the set of electrodes includes the voltage difference between the first location along the pipe and the second location along the pipe.

5. The system of claim 1, wherein the impedance characteristic of the fluid inside the pipe measured by the set of electrodes includes current between the first location along the pipe and the second location along the pipe.

6. The system of claim 1, wherein fluid flow regime inside the pipe is determined based on the multi-frequency measurement of the impedance characteristic of the fluid inside the pipe.

7. The system of claim 1, wherein the hydrocarbon concentration in the fluid includes percentage of oil and water in the fluid.

8. The system of claim 6, wherein the determination of the fluid flow regime inside the pipe includes identification of stratified flow, bubbly flow, or slug flow inside the pipe.

9. The system of claim 1, wherein the fluid composition of the fluid inside the pipe determined for different times is used to determine a dynamic characteristic of the fluid inside the pipe.

10. The system of claim 1, wherein the pipe is inside a horizontal well, and the fluid composition of the fluid inside the pipe determined for different locations is used to identify producing stages and non-producing stages inside the horizontal well.

11. A method for determining fluid characteristics, the method comprising:

generating a multi-frequency signal to induce voltage difference between a first location along a pipe and a second location along the pipe, the voltage difference induced for multi-frequency measurement of an impedance characteristic of fluid inside the pipe;

obtaining the multi-frequency measurement of the impedance characteristic of the fluid inside the pipe from a set of electrodes, the set of electrodes configured to measure the impedance characteristic of the fluid inside the pipe, the set of electrodes including a first electrode positioned at the first location along the pipe and a second electrode positioned at the second location along the pipe; and determining fluid composition of the fluid inside the pipe based on the multi-frequency measurement of the impedance characteristic of the fluid inside the pipe, the fluid composition of the fluid including hydrocarbon concentration in the fluid;

wherein:

responsive to the voltage difference being initially induced for the multi-frequency measurement of the impedance characteristics of the fluid using voltage input and the hydrocarbon concentration in the fluid being lower than a first threshold value, the inducement of the voltage difference is switched from using the voltage input to using current input; and responsive to the voltage difference being initially induced for the multi-frequency measurement of the impedance characteristics of the fluid using the current input and the hydrocarbon concentration in the fluid being higher than a second threshold value, the inducement of the voltage difference is switched from using the current input to using the voltage input.

12. The method of claim 11, wherein the multi-frequency signal includes a voltage chirp signal.

13. The method of claim 11, wherein the multi-frequency signal includes a current chirp signal.

14. The method of claim 11, wherein the impedance characteristic of the fluid inside the pipe measured by the set of electrodes includes the voltage difference between the first location along the pipe and the second location along the pipe.

15. The method of claim 11, wherein the impedance characteristic of the fluid inside the pipe measured by the set of electrodes includes current between the first location along the pipe and the second location along the pipe.

16. The method of claim 11, wherein fluid flow regime inside the pipe is determined based on the multi-frequency measurement of the impedance characteristic of the fluid inside the pipe.

17. The method of claim 11, wherein the hydrocarbon concentration in the fluid includes percentage of oil and water in the fluid.

18. The method of claim 16, wherein determining the fluid flow regime inside the pipe includes identifying stratified flow, bubbly flow, or slug flow inside the pipe.

19. The method of claim 11, wherein the fluid composition of the fluid inside the pipe determined for different times is used to determine a dynamic characteristic of the fluid inside the pipe.

20. The method of claim 11, wherein the pipe is inside a horizontal well, and the fluid composition of the fluid inside the pipe determined for different locations is used to identify producing stages and non-producing stages inside the horizontal well.

\* \* \* \* \*